United States Patent [19]

Lee et al.

[11] Patent Number: 4,855,442

[45] Date of Patent: Aug. 8, 1989

[54] SUBSTITUTED 3-HYDROXY PYRAZOLES

[75] Inventors: Len F. Lee, St. Charles; Kurt Moedritzer, Webster Groves; Michael D. Rogers, Maryland Heights, all of Mo.

[73] Assignee: Monsanto Company, St. Louis, Mo.

[21] Appl. No.: 175,461

[22] Filed: Apr. 13, 1988

[51] Int. Cl.$^4$ .............................. C07D 231/20
[52] U.S. Cl. ................... 548/365; 548/367; 71/92
[58] Field of Search ............... 548/375, 376, 377, 365, 548/367

[56] References Cited

U.S. PATENT DOCUMENTS

| | | | |
|---|---|---|---|
| 3,666,756 | 5/1972 | Fukumura et al. | 260/240 |
| 3,728,297 | 4/1973 | Hoffman et al. | 548/116 |
| 3,772,311 | 11/1973 | Arya | 546/279 |
| 3,952,098 | 4/1976 | Hoffman et al. | 514/94 |
| 4,084,955 | 4/1978 | Kornis et al. | 71/92 |
| 4,256,902 | 3/1981 | Boschi et al. | 548/365 |
| 4,355,159 | 10/1982 | Iqbal et al. | 548/105 |
| 4,382,948 | 5/1983 | Kurkov | 514/94 |
| 4,383,116 | 5/1983 | Haga et al. | 548/367 |
| 4,415,739 | 11/1983 | Haga et al. | 548/367 |
| 4,424,214 | 1/1984 | Okada et al. | 514/94 |
| 4,463,085 | 7/1984 | Mitsui et al. | 430/372 |
| 4,465,675 | 8/1984 | Aoyagi | 514/94 |
| 4,480,103 | 10/1984 | Ishikawa et al. | 548/365 |
| 4,483,918 | 11/1984 | Sakai et al. | 430/372 |
| 4,528,258 | 7/1985 | Kitaguchi et al. | 430/203 |
| 4,584,266 | 4/1986 | Hirose et al. | 430/555 |
| 4,657,579 | 4/1987 | Milzner et al. | 71/92 |
| 4,666,502 | 5/1987 | Seckinger et al. | 71/90 |

OTHER PUBLICATIONS

DeStevens et al., *J. Am. Chem. Soc.* 81, 6292 (1959).
Derwent Abstract of Japanese Patent 1169573 published 4-14-73.
Derwent Abstract of Japanese Patent 157504/55 pub. 12-8-80.
Derwent Abstract of Fed. Rep. of Germany Patent 2,337,293 published 6/74.
Sucrow et al., *Chem. Ber.* 112, 1712 (1979).
Jan et al., *Vestn. Slov. Kem. Drus.* p. 421 (1983).
Derwent Abstract of Fed. Rep. of Germany Patent 3032421 published 4-1-82.
Derwent Abstract of Japanses Patent 021373/57 published 2-4-82.
Derwent Abstract of European Patent Application 204242-A published 12-10-87.

*Primary Examiner*—Richard A. Schwartz
*Assistant Examiner*—Richard A. Sharpe
*Attorney, Agent, or Firm*—Robert B. Martin

[57] ABSTRACT

The present invention relates to a class of 5-haloalkyl-3-hydroxy-1-($C_{1-2}$ alkyl)pyrazoles useful as precursors for an active class of phenoxypyrazole herbicides.

15 Claims, No Drawings

SUBSTITUTED 3-HYDROXY PYRAZOLES

RELATED APPLICATION

This is a continuation-in-part of Ser. No. 059,431, filed June 8, 1987, now abandoned.

FIELD OF THE INVENTION

The present invention relates to a class of 5-substituted-3-hydroxy-1-($C_{1-2}$ alkyl)pyrazoles. These compounds are precursors for an active class of phenoxypyrazole herbicides.

BACKGROUND OF THE INVENTION

It has recently been discovered that certain 3-phenoxypyrazole herbicides are particularly useful in controlling hard-to-kill perennial weeds at very low application rates. These new herbicides are described and claimed in copending commonly assigned application U.S. Ser. No. 07/175,460. A particularly effective herbicide within this class is 5-trifluoromethyl-4-chloro-3-(3-methoxy-4-nitrophenoxy)-1-methylpyrazole. The present invention relates to a class of intermediates used in the production of compounds within this new class of herbicides.

It is an object of the present invention to provide a new class of intermediate compounds useful in the production of compounds within this new class of 3-phenoxypyrazole herbicides.

Other objects and advantages will become apparent from the following disclosure.

SUMMARY OF THE INVENTION

The present invention relates to a class of substituted 3-hydroxypyrazoles having the following formula:

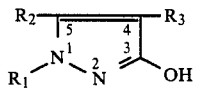

wherein:

$R_1$ is $C_{1-2}$ alkyl;

$R_2$ is $C_{1-2}$ haloalkyl, $C_{1-2}$ alkylsulfinyl or methoxymethyl; and $R_3$ is hydrido or halo.

The compounds of the present invention are used in the production of a class of highly active phenoxypyrazole herbicides. A more thorough disclosure of the present invention is presented in the detailed description which follows.

DETAILED DESCRIPTION OF THE INVENTION

The present invention relates to a class of substituted 3-hydroxypyrazoles having the following formula:

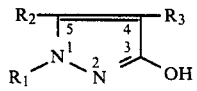

wherein:

$R_1$ is methyl or ethyl;

$R_2$ is halomethyl, haloethyl, methylsulfinyl, ethylsulfinyl, or methoxymethyl;

$R_3$ is hydrido or halo.

The term "$C_{1-2}$ alkyl" means a radical containing one or two carbon atoms. The term "haloalkyl" means an alkyl radical substituted with one or more halogen atoms preferably selected from bromo, chloro or fluoro, and more preferably fluoro.

Conveniently the pyrazoles may be prepared by reacting an alkylhydrazine with an alkyl 3-haloalkyl)-propynoate which is in turn prepared generally in accordance with procedures set forth in Huang et al. Scientia Sinica 25, 21 (1982) incorporated herein by reference. The Huang phosphorane intermediate can also be prepared by reacting (carbethoxymethyl)triphenylphosphonium bromide with trifluoroacetic anhydride in the presence of triethylamine and tetrahydrofuran.

The 5-trifluoromethyl-3-hydroxy-1-methylpyrazole may be conveniently prepared by reacting ethyl 4,4,4-trifluoro-2-butynoate with methylhydrazine in a suitable solvent such as methylene chloride or methanol/water at a low temperature from about $-78°$ C. to about $-20°$ C. The reaction at higher temperatures will result in a mixture of the 3-hydroxy and 5-hydroxypyrazole isomers. It is believed that reduced temperatures and more polar solvents provide greater amounts of the desired 3-hydroxy isomer of the pyrazole. The 3-hydroxypyrazole may be separated from the 5-hydroxypyrazole by stirring the isomer mixture product in an aqueous solution of sodium bicarbonate. The 5-hydroxy isomer is dissolved into solution while the 3-hydroxy isomer remains in suspension and is readily separated.

An alternative method of forming the 5-trifluoromethyl-3-hydroxy-1-methylpyrazole involves reacting ethyl 4,4,4-trifluoroacetoacetate in acetone with dimethyl sulfate in the presence of anhydrous potassium carbonate and preferably triethylmethylammonium methylsulfate to form 3-methoxy-4,4,4-trifluoro-2-butenoic acid ethyl ester. This ester is then reacted directly with methylhydrazine to form the 3- and 5-hydroxy isomer mixture of the pyrazole. The desired isomer can be separated as described above.

Another method of making 5-trifluoromethyl-3-hydroxypyrazole involves reacting the ethyl 4,4,4-trifluoroacetoacetate directly with the methylhydrazine in ether to form a mixture of the intermediates 5-hydroxypyrazolidin-3-one and 3-hydroxypyrazolidin-5-one and dehydration of these intermediates by the addition of sulfuric acid in chloroform to form a mixture of the 3- and 5-hydoxypyrazoles. The desired isomer can be separated as described above. Alternatively, 2,4,4 trifluoroacetoacetate can be reacted in a like manner to give 1-methyl-3-hydroxy-4-fluoro-5-difluoromethylpyrazole.

A preferred method of forming certain of the 3-hydroxypyrazoles of the present invention is shown in the Procedure illustrated on page 6 and involves bubbling ammonia gas through through the corresponding 4-halo-3-keto ester such as ethyl 4,4,4-trifluoroacetoacetate to form 3-amino-4,4,4-trifluoro-2-butenoic acid ethyl ester at an elevated temperature from about 55° to about 85° C. while removing water. This ester is then reacted directly with methylhydrazine at a temperature of about 40° C. to about 100° C. to form the 3- and 5-hydroxy isomer mixture of the intermediate pyrazole. The desired isomer can be separated as described above.

The 3-hydroxypyrazoles of the present invention having 5-$C_{1\ 2}$ alkylsulfinyl and 4-halo substituents are made by a two step process which comprises a first step of reacting methylhydrazine with methyl 2,3-dichloro-3-methylthioacrylate and potassium carbonate in a suitable solvent such as toluene. The reaction is conveniently conducted at reflux for a period of time of about 15 to about 20 hours to yield a solid product. The product from the first step is 5-methylthio-4-chloro-3-hydroxy-1-methylpyrazole. The pyrazole from step one can be oxidized by suitable oxidizing agents in a suitable solvent to form the corresponding 5-alkylsulfinylpyrazole. Conveniently the pyrazole is oxidized with one equivalent of m-chloroperbenzoic acid in dichloromethane.

The 3-hydroxypyrazoles of the present invention having 5-$C_{1-2}$ alkylsulfinyl and 4-hydrido substituents can be made by a 4 step process. The steps are as follows:

(i) reacting 1-methyl-3-alkylsilyloxypyrazole in anhydrous tetrahydrofuran with n-butyllithium at 78° C.;
(ii) adding dimethyldisulfide to the solution (i); and
(iii) reacting the resultant product of (ii) with HF in acetonitrile to form the corresponding 3-hydroxypyrazole having a 5-methylthio substituent which can be oxidized to the corresponding sulfinyl generally according with the above procedures.

The 5-methoxymethyl-4-chloropyrazole is made in a similar manner except the lithium salt of the pyrazole is reacted with bromomethylmethylether with subsequent desilylation.

Except as described below, other 3-hydroxypyrazoles of the present invention can be prepared generally in accordance with these procedures. The 1-ethylpyrazoles are also prepared generally in accordance with these procedures. The ethylhydrazine is conveniently liberated from its oxalate salt in situ with triethylamine during the reaction.

Procedure

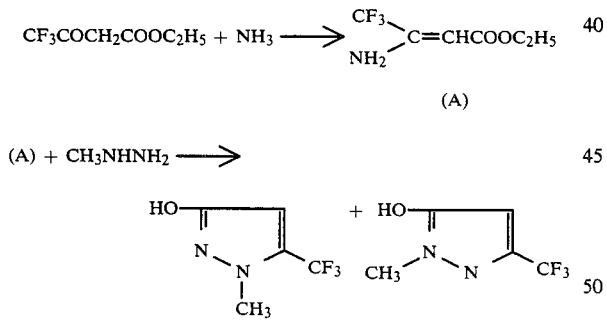

(A)

(A) + CH$_3$NHNH$_2$ ———>

The 5-haloalkyl-3-hydroxy-1-alkylpyrazoles can be chlorinated or brominated to form the corresponding 5-haloalkyl-4-(halo)-3-hydroxy-1-alkylpyrazoles. Suitable chlorinating/brominating agents include bromine, chlorine, sulfuryl chloride and sulfuryl bromide. Preferred chlorinating/brominating agents are 1,3-dichloro-5,5-dimethylhydantoin and 1,3-dibromo-5,5-dimethylhydantoin. The halogenation is conveniently accomplished by mixing the pyrazole at about room temperature with at least one equivalent of the halogenating agent in a suitable solvent (e.g. diethyl ether or ether/acetic acid mixture). The pyrazole is isolated by standard laboratory techniques.

The pyrazoles having a 4-fluoro, a 4-iodo or a 5-fluoromethyl substituent are made in a different manner. The pyrazole having a 4-fluoro substituent is made by reacting ethyl trifluoroacetate with ethyl fluoroacetate (neat) and a strong base such as sodium hydride to give ethyl 2,4,4,4-tetrafluoroacetoacetate which is sequentially reacted with (i) dimethyl sulfate in the presence of potassium carbonate and (ii) methylhydrazine to form the corresponding 4-fluoropyrazole. The 4-iodopyrazole is formed from the corresponding 4-bromopyrazole. In order to protect the 3-hydroxy group, the 4-bromopyrazole is reacted with trialkylsilyl chloride. The resulting 3-trialkylsiloxy-4-bromopyrazole is then sequentially reacted with (i) n-butyllithium at about −78° C. in THF; (ii) iodine and (iii) aqueous HF in acetonitrile to form the 4-iodopyrazole.

Pyrazoles with a 5-fluoromethyl substituent are made from the corresponding 5-methoxycarbonylpyrazole which is in turn prepared by reacting dimethyl acetylenedicarboxylate with methylhydrazine in ether. The 5-(methoxycarbonyl)pyrazole is sequentially reduced with lithium aluminum hydride and fluorinated with diethylaminosulfur trifluoride (DAST) to form the 5-fluoromethylpyrazole intermediate. The 5-trichloromethylpyrazole can be made by suitable processes known to those skilled in the art.

Those skilled in the art will appreciate that the 3-hydroxypyrazoles may exist in either of their tautomeric structures (the 3-hydroxypyrazole or the pyrazolidin-3-one) and the 3-hydroxypyrazole structure used herein is intended to mean both tautomeric structures.

To form compounds within the new class of phenoxypyrazole herbicides, a substituted 3-hydroxypyrazole of the present invention is reacted with a 4-halonitrobenzene having a suitable 2-substituent such as methoxy. The reaction is conveniently conducted in a suitable solvent such as DMSO in the presence of potassium carbonate.

The following examples are detailed descriptions of methods of preparations of certain compounds of the present invention. The detailed preparations fall within the scope of, and serve to exemplify, the more generally described methods of preparation set forth above. These examples are presented for illustrative purposes only and are not intended as a restriction on the scope of the invention. All parts are by weight unless otherwise indicated.

EXAMPLE 1

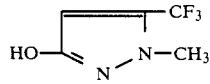

5-Trifluoromethyl-3-hydroxy-1-methylpyrazole (a) To a mixture of 55.20 g (0.3 mol) of ethyl 4,4,4-trifluoroacetoacetateand 50 ml of water was added at once 27.64 g (0.6 mol) of methylhydrazine. A violent reaction occurred and subsided. The mixture was held at reflux for 2 hours and cooled to room temperature overnight. Long needle crystals formed which were filtered to give 4.2 g of needles of the desired product, m.p. 129.5°–131.5° C.

Elemental Analysis of $C_5H_5F_3N_2O$

| | C | H | N |
|---|---|---|---|
| Calculated | 36.15 | 3.03 | 16.87 |
| Found | 36.17 | 3.07 | 16.91 |

EXAMPLE 2

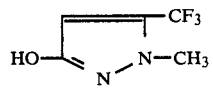

5-Trifluoromethyl-3-hydroxy-1-methylpyrazole

A flask was charged with 6 kg of ether and 6164.2 g (33.5 mol) of ethyl 4,4,4-trifluoroacetoacetate. With stirring 1542.4 g (33.5 mol) methylhydrazine was added. The temperature was maintained at about 24° C. during the addition. After one additional hour of stirring the reaction was complete. Solvent was stripped to remove most of the ether and the residue was then slurried in 12 l of chloroform with vigorous stirring. To the slurry was added 50 ml of concentrated sulfuric acid and the mixture was stirred overnight. An additional 100 ml of sulfuric acid was added and the slurry was washed once with 3 l of water and 5 times with 3 l of 10% sodium bicarbonate to remove the 5-hydroxy isomer and twice with 3 l of water. The aqueous layers and undissolved crystals were twice extracted sequentially with 4 l of chloroform. Chloroform was stripped on a rotary evaporator at 40° C. under vacuum to yield 1405.9 g (25.3% yield) of a solid, m.p. 130°–131° C.

EXAMPLE 3

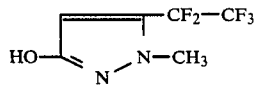

5-Pentafluoroethyl-3-hydroxy-1-methylpyrazole 62.03 g (0.25 mol) of 3-methoxy-3-pentafluoroethyl-2-propenoic acid ethyl ester was placed in a flask in ice water. 12.67 g (0.275 mol) of methylhydrazine was added with stirring keeping the temperature below 40° C. After the addition, the flask was removed from the ice bath and left standing for 3 days at ambient temperature. The reaction mixture was treated with 250 ml of aqueous sodium bicarbonate, washed with water, filtered and dried in vacuo to give 16.1 g (30% yield) of a white solid, m.p. 119°–124° C.

EXAMPLE 4

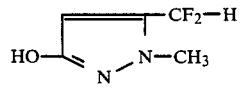

5-Difluoromethyl-3-hydroxy-1-methylpyrazole 10.2 g (0.068 mol) of ethyl 4,4-difluoro-2-butynoate in 20 ml of methylene chloride was added dropwise to a stirred solution of 4 ml (0.075 mol) of methylhydrazine in 80 ml of methylene chloride cooled to −78° C. The resultant reaction mixture was stirred overnight and subsequently concentrated in vacuo to afford 8.63 g of a clear, yellow oil. The oil was dissolved in ethyl acetate and washed with 10% aqueous sodium bicarbonate. The organic layer was dried, concentrated and recrystallized from carbon tetrachloride to give 2.2 g (21.7% yield) of a white crystalline solid, m.p. 115°–119° C.

Elemental Analysis for $C_5H_6N_2O_1F_2$

| | C | H | N |
|---|---|---|---|
| Calculated | 40.55 | 4.08 | 18.91 |
| Found | 40.47 | 4.11 | 18.86 |

EXAMPLE 5

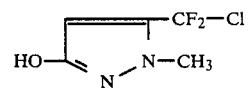

5-Chlorodifluoromethyl-3-hydroxy-1-methylpyrazole 50.14 g (0.25 mol) of 3-chlorodifluoromethyl-3-methoxypropenoic acid ethyl ester was placed in a flask in ice water. 12.67 g (0.275 mol) of methylhydrazine was added while stirring until the reaction mixture boiled. Additional methylhydrazine was added and the mixture was left standing overnight. The solvent was evaporated off and the residue recrystallized from hot methylcyclohexane to give 17.4 g of off-white solid, m.p. 122°–123° C.

Elemental Analysis for $C_5H_5ClF_2N_2O$

| | C | H | N |
|---|---|---|---|
| Calculated | 32.90 | 2.76 | 15.35 |
| Found | 33.24 | 2.82 | 15.66 |

EXAMPLE 6

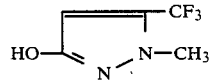

5-Trifluoromethyl-3-hydroxy-1-methylpyrazole 1.15 g (0.062 mol) of 3-amino-4,4,4-trifluoro-2-butenoic acid ethyl ester was cooled in an ice bath to form a solid. The ethyl ester was liquified upon the addition of 1.5 ml (0.038 mol) of methylhydrazine. The temperature was raised to 60° C. and the mixture was stirred for 6.5 hours. An N.M.R. spectrum of the crude mixture showed about 80% of the 3-hydroxy isomer and 10% of the 5-hydroxy isomer. The mixture was then evaporated on a rotary evaporator and stirred in saturated sodium bicarbonate solution, filtered, washed and dried to yield 2.1 g of a solid, m.p. 130°–131° C.

EXAMPLE 7

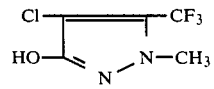

5-Trifluoromethyl-4-chloro-3-hydroxy-1-methyl-pyrazole 1907 g (11.48 mol) of 5-trifluoromethyl-3-hydroxy-1-methylpyrazole was stirred with 8 kg of ether and cooled to 0° C. 1222 g (6.2 mol) of 1,3-dichloro-5,5-dimethylhydantoin was added in three equal portions and the mixture was allowed to cool to 0° C. after each addition. The mixture was stirred for 4 hours, washed with water, brine and water. All washes were extracted with ether and the combined ether solutions were dried with MgSO₄, filtered, evaporated on a rotary evaporator and recrystallized from methylcyclohexane to give 2131 g of a tan solid, m.p. 136°–140° C.

Using procedures similar to those set out in detail above, further compounds of the present invention were prepared and are shown in the following Table I.

TABLE I

| Example Compound # | Name | Structure | Analysis (%) Calc'd | Found |
|---|---|---|---|---|
| 8 | 1H—pyrazol-3-ol, 4-chloro-1-1-methyl-5-(pentafluoroethyl)- MP:164.5–169.0 | 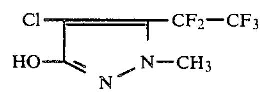 | C 28.76<br>H 1.61<br>N 11.18 | 29.36<br>1.67<br>11.46 |
| 9 | 1H—pyrazol-3-ol, 4-bromo-1-methyl-5-(trifluoromethyl)-MP:154.0–156.0 | 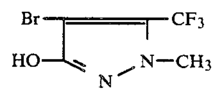 | C 24.51<br>H 1.65<br>N 11.43 | 24.58<br>1.69<br>11.47 |
| 10 | 1H—pyrazol-3-ol, 1-ethyl-5-(trifluoromethyl)- MP: 85.5–87.5 | 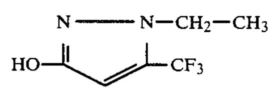 | C 40.01<br>H 3.92<br>N 15.55 | 40.09<br>3.96<br>15.54 |
| 11 | 1H—pyrazol-3-ol, 4-chloro-1-ethyl-5-(trifluoromethyl)- MP:135.0–137.0 | 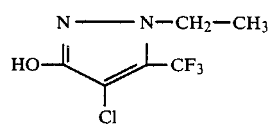 | C 33.58<br>H 2.82<br>N 13.06 | 33.78<br>2.82<br>13.29 |
| 12 | 1H—pyrazol-3-ol, 4-fluoro-1-methyl-5-(trifluoromethyl)- MP:101.5–102.5 | 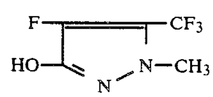 | C 32.62<br>H 2.19<br>F 41.28<br>N 15.22 | 32.62<br>2.23<br><br>15.31 |
| 13 | 1H—pyrazol-3-ol, 4-chloro-5-(chlorodifluoromethyl)-1-methyl- MP:128.0 | 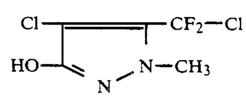 | C 27.67<br>H 1.86<br>Cl 32.67<br>F 17.51<br>N 12.91 | 27.78<br>1.86<br><br><br>12.91 |
| 14 | 1H—pyrazol-3-ol, 4-chloro-5-(difluoromethyl)-1-methyl- MP:171.0–173.0 | 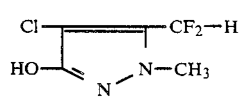 | C 32.90<br>H 2.76<br>Cl 19.42<br>F 20.81<br>N 15.35 | 33.14<br>2.78<br><br><br>15.46 |
| 15 | 1H—pyrazol-3-ol, 4-iodo-1-methyl-5-(trifluoromethyl)- MP:190.0–192.0 | 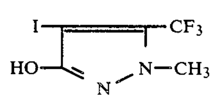 | C 20.57<br>H 1.38<br>F 19.52<br>I 43.46<br>N 9.59 | 21.09<br>1.45<br><br><br>9.77 |
| 16 | 1H—pyrazl-3-ol, 4-fluoro-5-(difluoromethyl)-1-methyl- MP:157.0–159.0 | 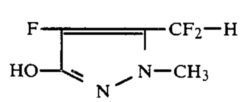 | C 36.15<br>H 3.03<br>F 34.32<br>N 16.86 | 36.23<br>3.03<br><br>16.84 |
| 17 | 1H—pyrazol-3-ol, 4-bromo-5-(difluoromethyl)-1-methyl- MP:200.0–203.0 | 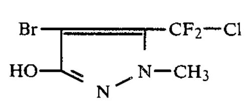 | C 26.45<br>H 2.22<br>Br 35.20<br>F 16.74<br>N 12.34 | 26.59<br>2.23<br><br><br>12.34 |

Although this invention has been described with respect to specific embodiment, the details thereof are not to be construed as limitations, for it will be apparent that various embodiments, changes, and modifications may be resorted to without departing from the spirit and scope thereof and it is understood that such equivalent embodiments are intended to be included within the scope of this invention.

We claim:

1. A compound represented by the formula:

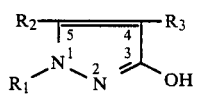

wherein:

$R_1$ is methyl or ethyl;

$R_2$ is halomethyl, haloethyl, methylsulfinyl, ethylsulfinyl or methoxymethyl $R_3$ is hydrido or halo.

2. A compound according to claim 1 wherein $R_1$ is methyl.

3. A compound according to claim 2 wherein $R_3$ is halomethyl.

4. A compound according to claim 3 wherein $R_2$ is trifluoromethyl or difluoromethyl.

5. A compound according to claim 4 wherein $R_3$ is halo.

6. A compound according to claim 5 wherein $R_3$ is chloro.

7. A compound represented by the formula:

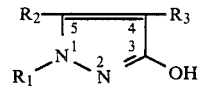

wherein:

$R_1$ is methyl or ethyl;

$R_2$ is halomethyl or haloethyl; and $R_3$ is hydrido or halo.

8. A compound according to claim 7 wherein $R_1$ is methyl.

9. A compound according to claim 8 wherein $R_3$ is chloro or bromo.

10. A compound according to claim 9 wherein $R_2$ is difluoromethyl.

11. A compound according to claim 9 wherein $R_2$ is trifluoromethyl.

12. The compound 5-trifluoromethyl-4-chloro-3-hdyroxy-1-methylpyrazole.

13. The compound 5-trifluoromethyl-3-hydroxy-1-methylpyrazole.

14. The compound 5-difluoromethyl-3-hydroxy-1-methylpyrazole

15. The compound 5-difluoromethyl-4-chloro-3-hydroxy-1-methylpyrazole.

* * * * *